United States Patent
Helfenbein et al.

(10) Patent No.: US 10,271,767 B2
(45) Date of Patent: Apr. 30, 2019

(54) AUTOMATED SPIROGRAM ANALYSIS AND INTERPRETATION

(75) Inventors: Eric Helfenbein, Sunnyvale, CA (US); Sophia Huai Zhou, Briarcliff Manor, NY (US); Martin Mason, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 655 days.

(21) Appl. No.: 13/980,384

(22) PCT Filed: Jan. 24, 2012

(86) PCT No.: PCT/IB2012/050316
§ 371 (c)(1),
(2), (4) Date: Jul. 18, 2013

(87) PCT Pub. No.: WO2012/104743
PCT Pub. Date: Aug. 9, 2012

(65) Prior Publication Data
US 2013/0303932 A1   Nov. 14, 2013

Related U.S. Application Data (60) Provisional application No. 61/437,806, filed on Jan. 31, 2011.

(51) Int. Cl.
*A61B 5/08* (2006.01)
*A61B 5/091* (2006.01)
(Continued)

(52) U.S. Cl.
CPC .............. *A61B 5/091* (2013.01); *A61B 5/087* (2013.01); *A61B 5/097* (2013.01); *A61B 5/7221* (2013.01); *A61B 5/7278* (2013.01); *A61B 5/7475* (2013.01)

(58) Field of Classification Search
CPC .................................................... A61B 5/087
See application file for complete search history.

(56) References Cited

U.S. PATENT DOCUMENTS 3,991,304 A    11/1976   Hellsman
4,893,632 A *   1/1990   Armington ........ A61B 5/04525
                                            600/509

(Continued)

FOREIGN PATENT DOCUMENTS

CN         1486160 A      3/2004
CN        10143913 A      9/2007

(Continued)

OTHER PUBLICATIONS

Carroll, Spirometry: Making sense of the tracings, 2003, Web, Retrieved from: http://www.modernmedicine.com/modern-medicine/content/spirometry-making-sense-tracings.*

(Continued)

*Primary Examiner* — Christian Jang
(74) *Attorney, Agent, or Firm* — Michael W. Haas (57) ABSTRACT

Automated analysis and interpretation of spirograms is provided to assess lung function of a subject. If the shape of a spirogram plot is deemed suitably reliable, the spirogram may be subsequently used for diagnostic purposes. Quality control of spirograms and/or interpretation of reliable spirograms may use shape templates corresponding to common test problems and/or typical lung diseases.

15 Claims, 6 Drawing Sheets

(51) Int. Cl.
*A61B 5/00* (2006.01)
*A61B 5/087* (2006.01)
*A61B 5/097* (2006.01)

(56) References Cited

U.S. PATENT DOCUMENTS

| | | | |
|---|---|---|---|
| 5,137,026 A * | 8/1992 | Waterson | A61B 5/09 600/538 |
| 5,562,101 A | 10/1996 | Hankinson et al. | |
| 5,634,468 A * | 6/1997 | Platt | A61B 5/0006 128/903 |
| 2003/0013946 A1* | 1/2003 | Schau | A61B 5/087 600/300 |
| 2004/0127949 A1* | 7/2004 | Kim | A61N 1/3712 607/27 |
| 2004/0267321 A1* | 12/2004 | Boileau | A61B 5/04525 607/3 |
| 2005/0182337 A1* | 8/2005 | Botbol | A61B 7/003 600/538 |
| 2005/0217674 A1* | 10/2005 | Burton | A61B 5/04 128/204.23 |
| 2007/0060831 A1* | 3/2007 | Le | A61B 5/0476 600/544 |
| 2007/0191726 A1 | 8/2007 | Harnoncourt | |
| 2009/0159082 A1* | 6/2009 | Eger | A61B 5/0488 128/204.23 |
| 2009/0270751 A1 | 10/2009 | Peng | |
| 2012/0029376 A1* | 2/2012 | Meng | A61B 5/087 600/538 |

FOREIGN PATENT DOCUMENTS

| | | |
|---|---|---|
| DE | 102007012330 A1 | 9/2008 |
| EP | 1374767 A2 | 1/2004 |
| JP | H08173404 A | 7/1996 |
| JP | 2006068533 A | 3/2006 |
| JP | 2007029258 A | 2/2007 |
| WO | 199841146 | 9/1998 |
| WO | WO9841146 A1 | 9/1998 |
| WO | WO0176455 A2 | 10/2001 |
| WO | WO2006079152 A1 | 8/2006 |
| WO | WO2010150239 A1 | 12/2010 |

OTHER PUBLICATIONS

Johns et al, Spirometry: The Measurement and Interpretation of Ventilatory Function in Clinical Practice, 2008, Web, Retrieved from: http://www.nationalasthma.org.au/uploads/content/211-spirometer_handbook_naca.pdf.*
Uosherc et al, NIOSH Spirometry Training Guide, 2003, Web, Retrieved from: https://www.cdc.gov/niosh/docs/2004-154c/pdfs/2004-154c.pdf.*
Mark L. Levy et al; "Diagnostice Spirometry in Primary Care", Primary Care Respiratory Journal, 2009, vol. 18, No. 3, pp. 130-147.
Kevin McCarthy; "Plumonary Function Testing", Cleveland Clinic, Center for Continuing Education, Disease Management Project, pp. 1-17, Aug. 1, 2010.
Dr. Alan Kaplan et al; "Spirometry", IPCRG Opinion No. 1, GPIAG Opinion No. 7, International Primary Care Respiratory Group, pp. 1-2, Nov. 2003.
"Spirometry", pp. 1-5 Source: http://www.ebme.co.uk/arts/spiro/.

* cited by examiner

AUTOMATED SPIROGRAM ANALYSIS AND INTERPRETATION

The present disclosure pertains to machine-assisted analysis and interpretation of spirograms.

It is well known to use spirometry as a way to assess lung function. By measuring maximum forced expiratory volume of a patient (a.k.a. a subject), a trained medical professional may diagnose a variety of conditions affecting the breathing of the subject. Commonly used spirometers may be employed to derive such quantitative measurements as forced vital capacity (FVC: total volume of air that can be forcibly exhaled in one breath), forced expiratory volume in one second (FEV1: volume of air expired in the first second of one breath), and the ratio of FEV1 over FVC. Subjects are asked to breathe in as deeply as possible, and exhale forcibly using maximum effort. Some spirometers are able to produce diagrams (a.k.a. plots) depicting the expiration by the subject, e.g. a volume-time plot and/or a flow-volume plot. Both types of plot represent expiratory volume during the expiration, and are usually referred to as spirograms.

An improperly administered or executed test may result in inferior measurements and/or plots, which may in turn negatively affect the quality of any diagnosis relying on them. Considerable knowledge is required to adequately use spirometers and interpret the resulting measurements. Accordingly, there is a need for improved ease of use, both for administering a spirometry test, as well as interpreting the measurements from a properly administered spirometry test, in particular its spirograms.

Accordingly, it is an object of one or more embodiments of the present invention to provide a method for assessing lung function of a subject, the method being implemented in a diagnostic device configured to execute one or more computer program modules. In one embodiment, the method comprising receiving expiratory airflow from the airway of the subject during an expiration by the subject; measuring, from the received expiratory airflow, expiratory volume during the expiration by the subject; creating a plot representing expiratory volume during the expiration, wherein the plot has a shape; determining the reliability of the measured expiratory volume during the expiration in assessing lung function of the subject; and assessing, based on the shape of the plot, lung function characteristics of the subject.

It is yet another aspect of one or more embodiments of the present invention to provide a system for assessing lung function of a subject having an airway. In one embodiment the system comprises a mouthpiece, a sensor, and one or more processors. The mouthpiece is configured to receive expiratory airflow from the airway of a subject during an expiration by the subject. The sensor is configured to measure expiratory volume from the received expiratory airflow. The one or more processors are configured to execute computer program modules including a plotting module, a reliability, an analysis module, and an assessment module. The plotting module is configured to create a plot representing the expiratory volume during the expiration, wherein the plot has a shape. The reliability module is configured to determine a reliability quantifier of the measured expiratory volume in assessing lung function of the subject. The analysis module is configured to analyze the measured expiratory volume by determining one or more of an initial expiratory volume of a first period of the expiration, or a total expiratory volume of the expiration. The assessment module is configured to assess lung function characteristics of the subject based on data received from the analysis module.

It is yet another aspect of one or more embodiments to provide a system configured to assess lung function of a subject. In one embodiment, the system comprises means for receiving expiratory airflow from the airway of the subject during an expiration by the subject; means for measuring, from the received expiratory airflow, expiratory volume during the expiration by the subject; means for creating a plot representing expiratory volume during the expiration, wherein the plot has a shape; means for determining, based on the expiratory volume during the expiration, the reliability of the measured expiratory volume during the expiration in assessing lung function of the subject; and means for assessing, based on the shape of the plot, lung function characteristics of the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
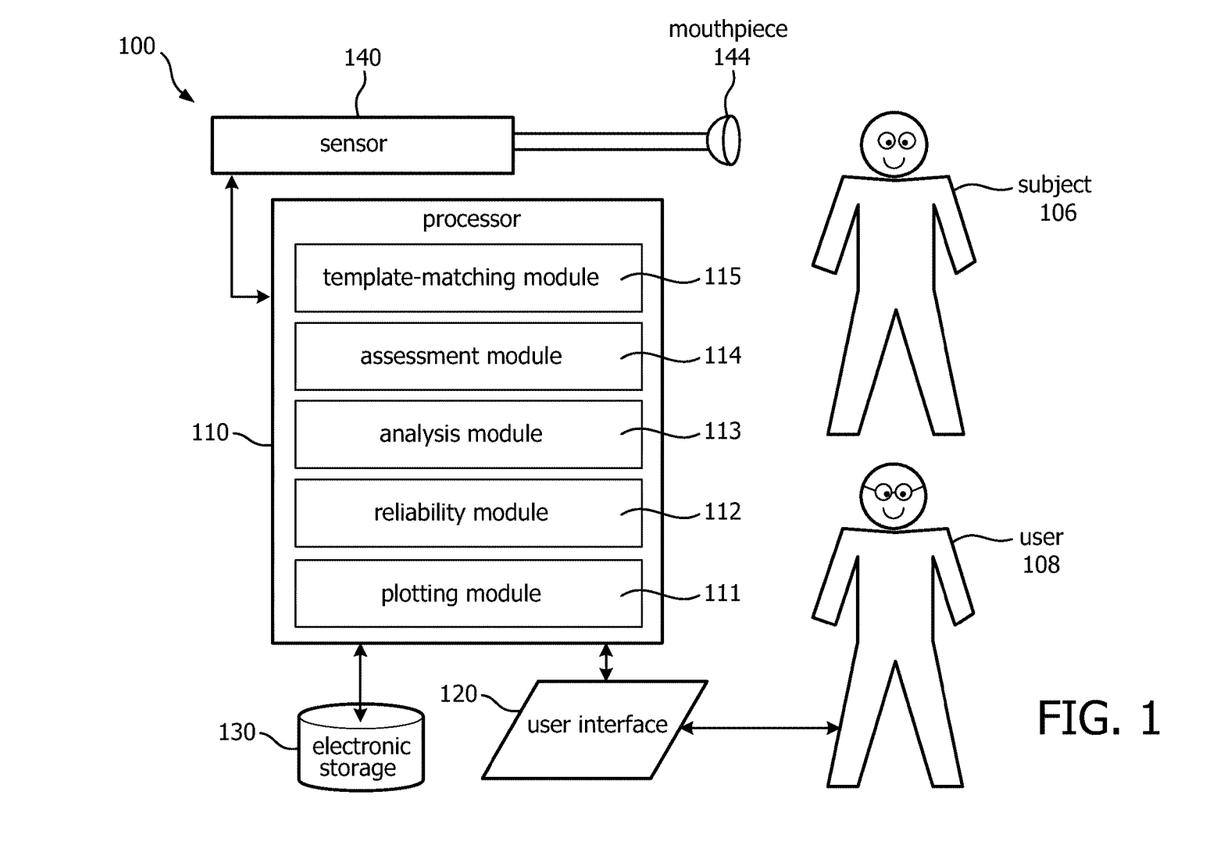
FIG. 1 schematically illustrates a system configured to assess lung function of a subject, a subject, and a user.

FIG. 1 schematically illustrates a system 100 configured to assess lung function of a subject, a subject, and a user. In particular, system 100 receives, measures, and plots expiratory airflow from the airway of a subject during an expiration by the subject. The reliability of a (spirogram) plot is determined, before assessing lung function characteristics based on the measured expiratory volume and/or the shape of the plot. In one embodiment, system 100 comprises one or more of a processor 110, a user interface 120, an electronic storage 130, a sensor 140, a mouthpiece 144, and/or other components. To administer a test, a subject exhales into mouthpiece 144 of system 100, causing sensor 140 to detect and measure airflow—much like a standard spirometer. One or more modules within processor 110 proceed to create a plot from the measured airflow. Subsequently, the reliability of the created plot is determined. Then, after the plot is deemed reliable, automated interpretation and/or a diagnosis of the results is provided Mouthpiece 144 is configured to receive expiratory airflow from the airway of a subject 106 during expiration by the subject. Sensor 140 is configured to measure, from the received expiratory airflow, expiratory volume during the expiration by the subject. Mouthpiece 144 is in fluid communication with sensor 140. Plotting module 111 is configured to create a plot, representing the measured expiratory volume during the expiration by the subject. Measurements of the received expiratory airflow may also include one or more of flow, pressure, humidity, velocity, acceleration, and/or other parameters related to expiratory airflow. System 100 may additionally be configured to measure and plot inspiratory airflow of a subject for a range of parameters similar to those given for expiratory airflow. The plots for expiratory airflow and inspiratory airflow can be combined, e.g. in a flow-volume plot.

Electronic storage 130 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. Electronic storage 130 may be a separate component within system 100, or electronic storage 130 may be provided integrally with one or more other components of system 100 (e.g., processor 110).

User interface 120 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer. Note that the subject and the user of system 100 may be one and the same person.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

The illustration of sensor 140 as including a single member in FIG. 1 is not intended to be limiting. In one embodiment sensor 140 includes a plurality of sensors operating as described above. Resulting signals or information from sensor 142 may be transmitted to processor 110, user interface 120, and/or electronic storage 130. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units. These processing units may be physically located within the same device, or processor 110 may represent processing functionality of a plurality of devices operating in coordination. For example, in some embodiments, the functionality attributed herein to processor 110 is performed by a first set of one or more processors disposed within a handheld device used to receive airflow at or near the airway of subject 106 and a second set of one or more processors located in a more robust computer platform (e.g., a personal computer, a handheld computer, a smart phone, a personal digital assistant, and/or other computer platforms) in at least intermittent communication with the handheld device (e.g., through a docking station, through wireless communication media, through a cable or communication port, etc.).

As is shown in FIG. 1, processor 110 is configured to execute one or more computer program modules. The one or more computer program modules include one or more of a plotting module 111, a reliability module 112, an analysis module 113, an assessment module 114, and a template-matching module 115, and/or other modules. Processor 110 may be configured to execute modules 111, 112, 113, 114, and/or 115 by software; hardware; firmware; some combination of software, hardware, and/or firmware; and/or other mechanisms for configuring processing capabilities on processor 110.

It should be appreciated that although modules 111, 112, 113, 114, and 115 are illustrated in FIG. 1 as being co-located within a single processing unit, in implementations in which processor 110 includes multiple processing units, one or more of modules 111, 112, 113, 114, and/or 115 may be located remotely from the other modules. The description of the functionality provided by the different modules 111, 112, 113, 114, and/or 115 described below is for illustrative purposes, and is not intended to be limiting, as any of modules 111, 112, 113, 114, and/or 115 may provide more or less functionality than is described. For example, one or more of modules 111, 112, 113, 114, and/or 115 may be eliminated, and some or all of its functionality may be provided by other ones of modules 111, 112, 113, 114, and/or 115. Note that processor 110 may be configured to execute one or more additional modules that may perform some or all of the functionality attributed below to one of modules 111, 112, 113, 114, and/or 115.

Plotting module 111 is configured to create one or more plots representing the expiratory and/or inspiratory volume during an expiration and/or inspiration by the subject. The plot(s) may depict the inspiratory and/or expiratory volume over time. For example, as is discussed further herein, the plotting module may be configured to create volume-time plots (see FIG. 2 for examples using only expiratory airflow), flow-volume plots (see FIG. 3 for examples using only expiratory airflow), and/or other types of plots representing the expiratory and/or inspiratory volume of subject 106. Plotting module 111 may share plots with other computer program modules, and/or electronic storage 130. Plots and/or any information based on the plots may be conveyed to a user via user interface 120.

Reliability module 112 is configured to determine a reliability quantifier of the expiratory and/or inspiratory volume as measured by sensor 140 in assessing lung function and/or diagnosing other respiratory health and/or functionality. The reliability quantifier may be based on a plot representing the expiratory and/or inspiratory volume, such as a plot created by plotting module 111. Reliability module 112 may simply indicate a good or bad quality of a measurement or plot. For example, if a subject coughs during the spirometry test, any measurement—including FVC and FEV1—or plot is obviously of bad quality in that its reliability in assessing lung functionality and/or for other diagnostic purposes will be low. Thus, such a plot is not suitable for subsequent usage, including diagnostic purposes. In some embodiments, reliability module 112 grades the reliability of a series of plots taken over a plurality of breaths by subject 106, e.g. numerically. This gradation of the series of plots may be used such that the most reliable plot or plots, i.e. the plot or plots with the highest quality, are used subsequently in system 100 and/or by the user. Alternatively, and/or simultaneously, reliability module 112 may determine whether a plot is suitably reliable, for example by comparing its graded reliability to a threshold. The threshold may be user-configurable (e.g., by subject 106, by a caregiver, by a therapy decision-maker, by a researcher, etc.), may be preset at manufacture, may be determined based on subject parameters, and/or may be determined through other techniques.

In some embodiments, the operation of reliability module 112 is based on point analysis. For example, reliability module 112 could determine the relative locations within a plot of the 25%, 50%, and 75% marks of peak expiratory flow and/or other measurements. Other percentages could be used as an alternative.

In some embodiments, the operation of reliability module 112 is based on shape analysis of the plot created by plotting module 111, e.g. by comparing the shape of a plot to a set of shape templates. This functionality may be included in reliability module 112 and/or in a dedicated module, such as template-matching module 115. The set of shape templates may include templates for different types of test problems, including e.g. coughing during the test. Such shape templates correspond to unreliable measurements of expiratory volume. If the shape of a plot sufficiently matches the shape template of a type of test problem, the plot may be deemed unreliable by reliability module 112 for subsequent (diagnostic) usage (in system 100). A user of system 100 may be notified immediately after administering a spirometry test that the results are unsuitable for diagnostic purposes, for example via a warning signal conveyed through user interface 120.

Figure 4A:
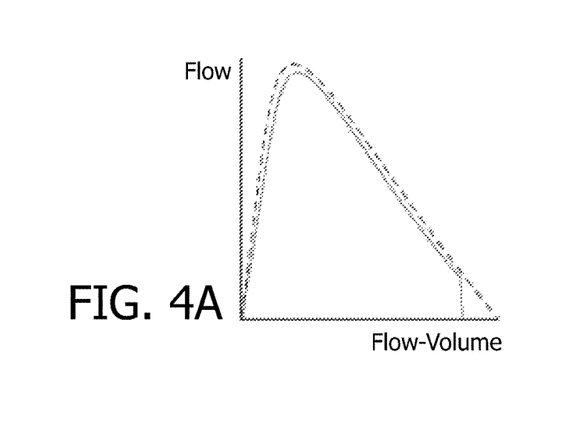
FIGS. 4A, 4B, 4C, and 4D illustrate flow-volume plots for various test problems related to administering spirograms.
Figure 4B:
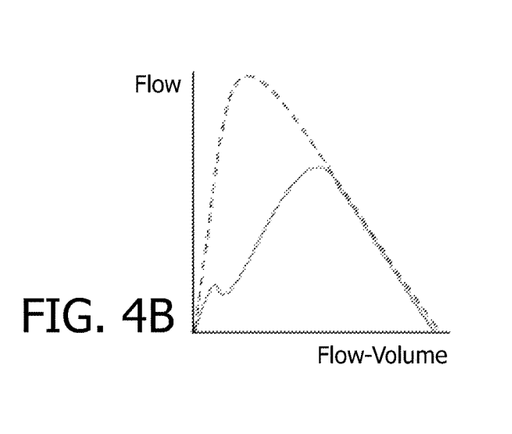
Figure 4C:
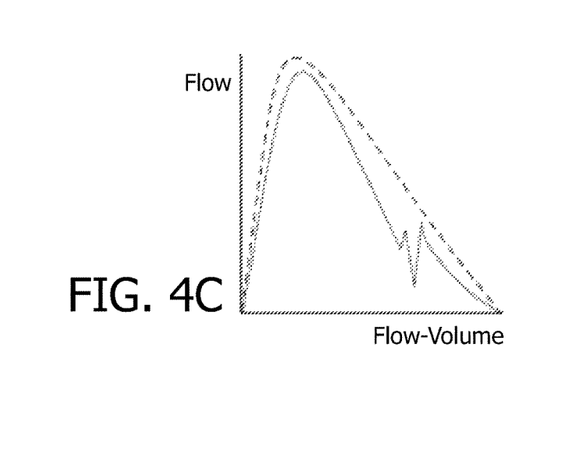
Figure 4D:
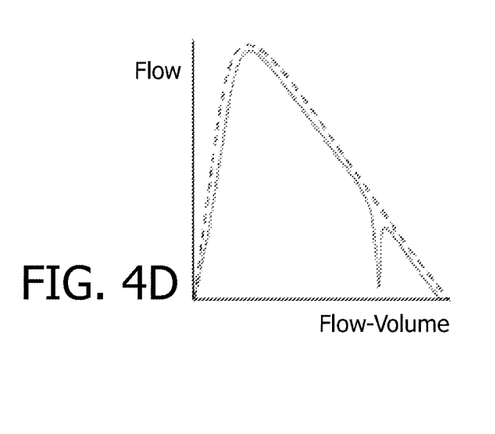

By way of illustration, FIGS. 4A, 4B, 4C, and 4D illustrate flow-volume plots for various types of test problems related to administering spirometric tests. These types of test problems indicate that a plot is not suitably reliable for subsequent usage in system 100, in particular for assessing lung function and/or diagnostic purposes. The Y-axis illustrates airflow, e.g. in liters per second. The dotted line indicates the expected plot for expiratory volume by a healthy subject (as far as lung disorders are concerned). FIG. 4A illustrates a flow-volume plot indicating premature finish of the expiratory effort by the subject. FIG. 4B illustrates a flow-volume plot indicating hesitation by the subject during the expiratory effort. FIG. 4C illustrates a flow-volume plot indicating a cough by the subject during the expiratory effort. FIG. 4D illustrates a flow-volume plot indicating premature finish coupled with a restart of the expiratory effort by the subject. System 100 thus automates quality control of administered spirometric tests.

Analysis module 113 is configured to analyze a plot representing expiratory and/or inspiratory volume of a subject by determining one or more of the FEV1 or the FVC. Alternatively, and/or simultaneously, the operation of analysis module 113 is based on information received from sensor 140.

Assessment module 114 is configured to assess lung function characteristics of a subject based on data received from analysis module 113. Alternatively, and/or simultaneously, the operation of assessment module 114 is based on shape analysis of the plot created by plotting module 111, e.g. by comparing the shape of a plot to a set of shape templates. This functionality may be included in assessment module 114 and/or in a dedicated module, such as template-matching module 115. Assessment by assessment module 114 may be performed responsive to a determination—such as performed by reliability module 112—that the measured expiratory volume during expiration is suitably reliable. Assessed lung function characteristics may pertain to obstructive lung diseases, including asthma, asthmatic bronchitis, chronic obstructive pulmonary disease (COPD), chronic obstructive bronchitis, cystic fibrosis, emphysema, and/or other obstructive lung diseases. Assessed lung function characteristics may also pertain to restrictive lung diseases, including Beryllium disease, congestive heart failure, idiopathic pulmonary fibrosis, infectious inflammation, interstitial pneumonitis, neuromuscular diseases, sarcoidosis, thoracic deformities, and/or other restrictive lung diseases.

Figure 2A:
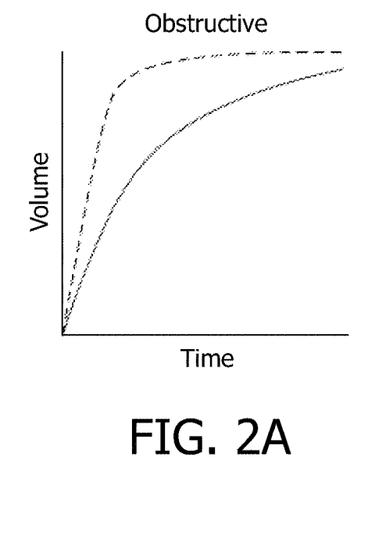
FIGS. 2A, 2B, and 2C illustrate volume-time plots for various classes of lung diseases.
Figure 2B:
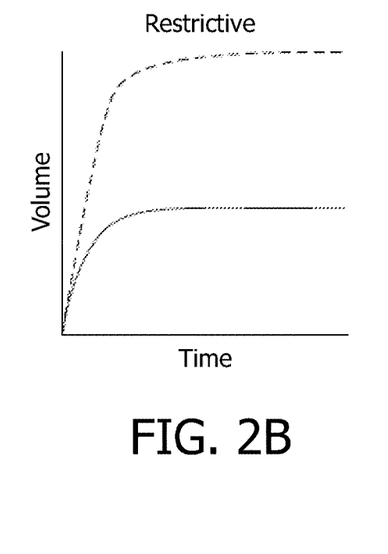
Figure 2C:
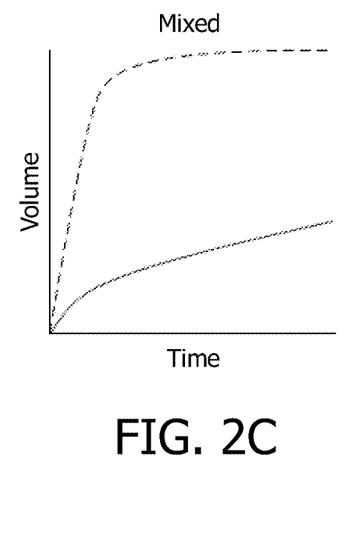

For example, assessment module 114 may instruct template-matching module 115 to compare the shape of a particular plot created by plotting module 111, which has been deemed suitably reliable by reliability module 112, to a second set of shape templates. This second set of shape templates may include a shape template for each of a variety of characteristic lung diseases, including obstructive lung diseases, restrictive lung diseases, combined obstructive-restrictive lung diseases, and/or other lung diseases. By way of illustration, FIGS. 2A, 2B, and 2C illustrate volume-time plots for various classes of lung diseases. In each figure, the dotted line indicates the expected plot for expiratory volume by a healthy subject (as far as lung disorders are concerned), which may be adjusted based on one or more of the subject's gender, age, height, weight, ethnic background, and/or other personal characteristics. FIG. 2A illustrates a typical volume-time plot for an obstructive lung disease, which is characterized by a total volume at or—more typically—just below the expected total volume at the end of a test, but a relatively gentler slope. FIG. 2B illustrates a typical volume-time plot for a restrictive lung disease, which is characterized by a total volume well below the expected total volume at the end of a test, but a relatively steep slope. FIG. 2C illustrates a typical volume-time plot for a combined obstructive-restrictive lung disease, which is characterized by a total volume well below the expected total volume at the end of a test, as well as a relatively gentler slope. Template-matching module 115 and/or assessment module 114 may, in the course of matching a particular plot or assessing the shape of a particular plot, advantageously determine one or more of an angle of a first specified section of the plot, a slope and/or derivative of a second specified section of the plot, a concavity of a first specified curve in the plot, a convexity of a second specified curve in the plot, or a measure of smoothness for (a particular part of) the plot. Any of these shape characteristics, alone or in combination, may be used to identify lung function characteristics.

Template-matching module 115 is configured to compare the shape of a particular plot against a set of shape templates. Template-matching module 115 may be instructed, e.g. by reliability module 112 and/or assessment module 114, to perform a function regarding a particular plot. Template-matching module 115 may include multiple sets of shape templates, whose usage depends on the function template-matching module 115 is performing. For example, template-matching module 115 may indicate or return the shape template that most closely matches the shape of the particular plot. This shape template may be referred to as the optimal shape template for that particular plot, in consideration of a particular set of shape templates. In some embodiments, template-matching module 115 may be instructed to determine either a quantifier indicating how well the optimal shape template matches a particular plot or a quantifier indicating one or more deviations of the particular plot from the optimal shape template. Such determined quantifiers may be compared with a threshold value.

A set of shape templates that may be useful in conjunction with reliability module 112 include a shape template for each of a variety of spirometric test problems, including sub-maximal expiratory or inspiratory effort, a delay in initiation of expiration or inspiration, a shortening of expiratory duration, a delay in reaching maximum expiratory flow rate, coughing during expiration or inspiration, inspiration during the measuring of expiratory volume and vice versa, glottic obstruction of the mouthpiece, air leakage around the mouthpiece, and/or other spirometric test problems.

A set of shape templates that may be useful in conjunction with assessment module 114 may include a shape template for each of a class of lung diseases, including obstructive and restrictive lung disease, and/or each of a type of lung disease, including emphysema and neuromuscular weakness.

Figure 3A:
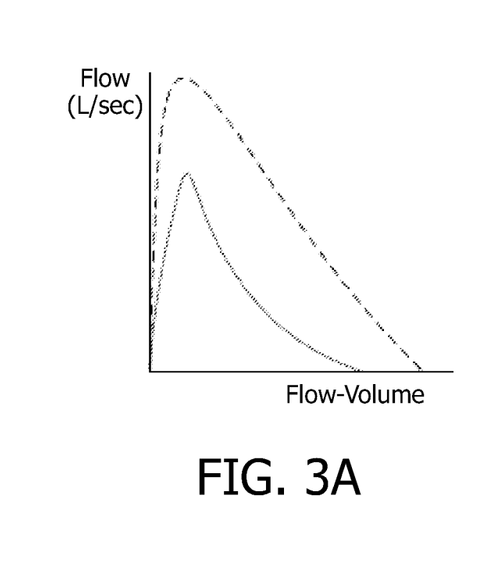
FIGS. 3A, 3B, and 3C illustrate flow-volume plots for various classes of lung diseases.
Figure 3B:
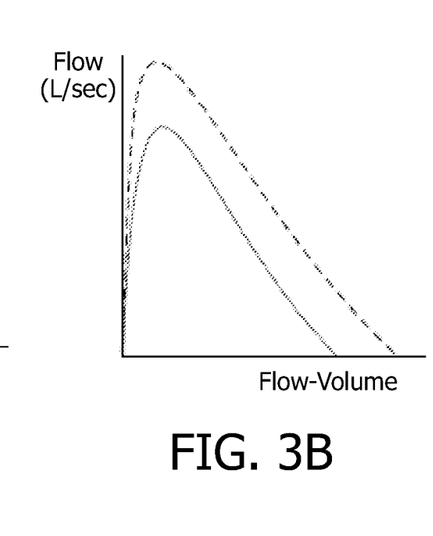
Figure 3C:
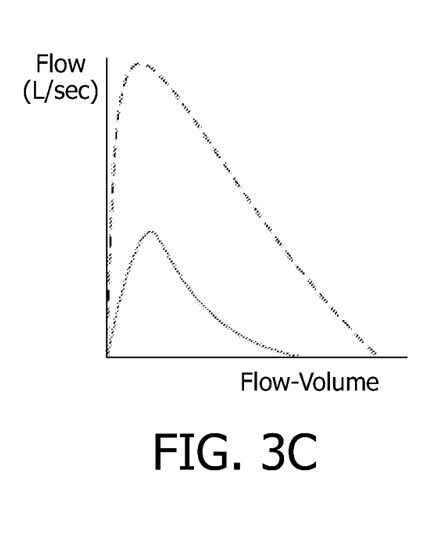

By way of illustration, FIGS. 3A, 3B, and 3C illustrate flow-volume plots for various classes of lung diseases. As in FIGS. 2A, 2B, and 2C, the dotted line indicates the expected plot for expiratory volume by a healthy subject. Template-matching module 115 may operate on flow-volume plots, using flow-volume shape templates. FIG. 3A illustrates a typical flow-volume plot for an obstructive lung disease, which is characterized by a reduced peak expiratory flow and a distinctive dipping (or concave) curve. FIG. 3B illustrates a typical flow-volume plot for a restrictive lung disease, which is characterized by a reduced volume, but generally a shape similar to the expected shape. FIG. 3C illustrates a typical flow-volume plot for a combined obstructive-restrictive lung disease. The typical flow-volume plots of FIGS. 3A, 3B, and 3C may be used as shape templates by template-matching module 115, for example in conjunction with assessment module 114. Template-matching module 115 and/or assessment module 114 may, in the course of matching a particular plot or assessing the shape of a particular plot, determine one or more of an angle of a first specified section of the plot, a slope of a second specified section of the plot, a concavity of a first specified curve in the plot, or a convexity of a second specified curve in the plot.

Figure 5A:
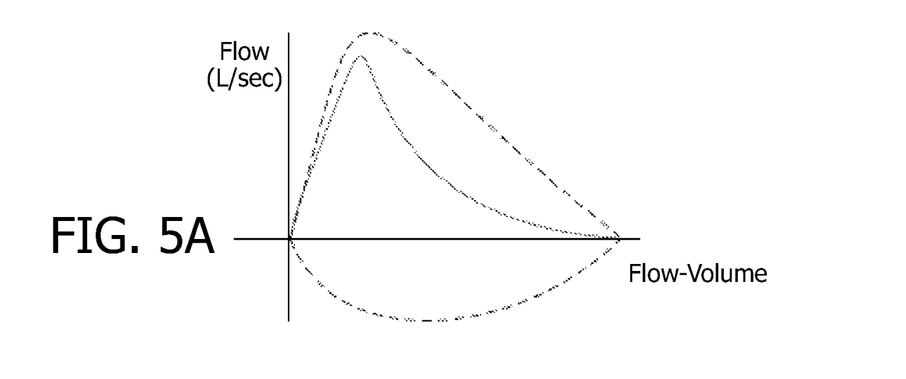
FIGS. 5A, 5B, and 5C illustrate flow-volume plots for various types of lung diseases.
Figure 5B:
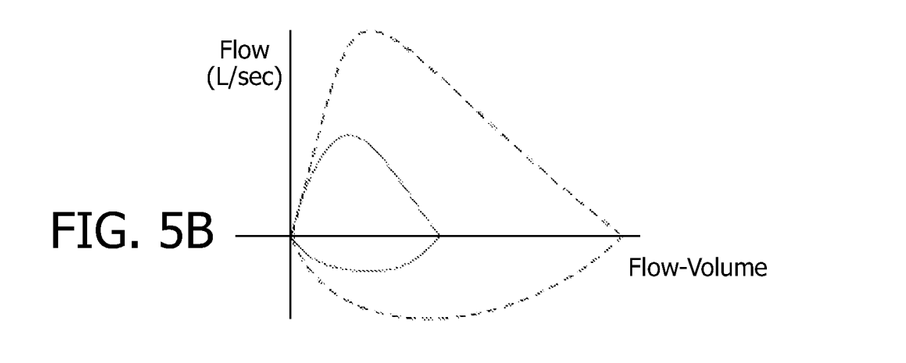
Figure 5C:
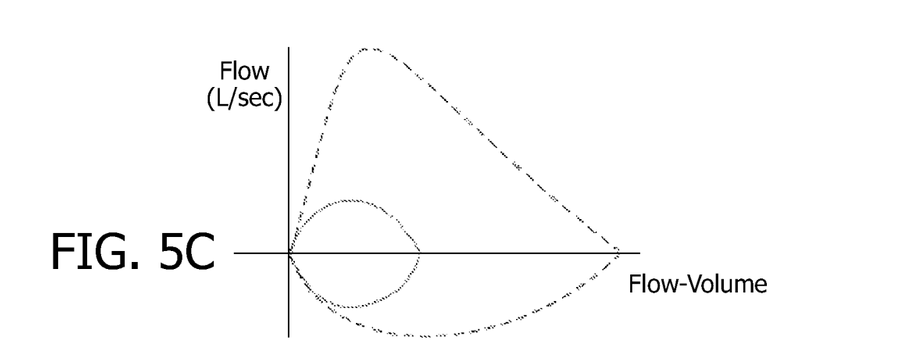

By further way of illustration, FIGS. 5A, 5B, and 5C illustrate flow-volume plots for various types of lung diseases. The X-axis illustrates volume, e.g. in liters. The curve below the X-axis indicates an inspiration, whereas the curve above the X-axis indicates, like before, an expiration. Similar to FIGS. 2A, 2B, and 2C, the dotted line indicates the expected plot for expiratory and/or inspiratory volume by a healthy subject. FIG. 5A illustrates a typical flow-volume plot for emphysema, which is characterized by a distinctive dipping (or concave) expiratory curve. Note that the inspiratory curve coincides in FIG. 5A with the expected curve. FIG. 5B illustrates a typical flow-volume plot for unilateral main-stem bronchial obstruction. FIG. 5C illustrates a typical flow-volume plot for neuromuscular weakness. The typical flow-volume plots of FIGS. 5A, 5B, and 5C may be used as shape templates by template-matching module 115, for example in conjunction with assessment module 114. System 100 thus automates (diagnostic) interpretation of spirograms.

Template-matching module 115 may include shape templates that can be adjusted based on one or more of the subject's gender, age, height, weight, ethnic background, and/or other personal characteristics. The adjustment may be implemented by using multiple shape templates per spirometric test problem or lung disease, derived formulas approximating a particular shape, a look-up table, and/or other ways to implement the adjustment of shape templates.

The disclosure may also be used to assess lung function of a single subject over a period of time. This period could span pre- and post-bronchodilator usage. Alternatively, this period could span days, weeks, months, and/or other durations during which the effects of a (therapeutic) treatment are tracked, as they pertain to lung function and/or lung function characteristics such as the ones discussed in this disclosure.

Figure 6:
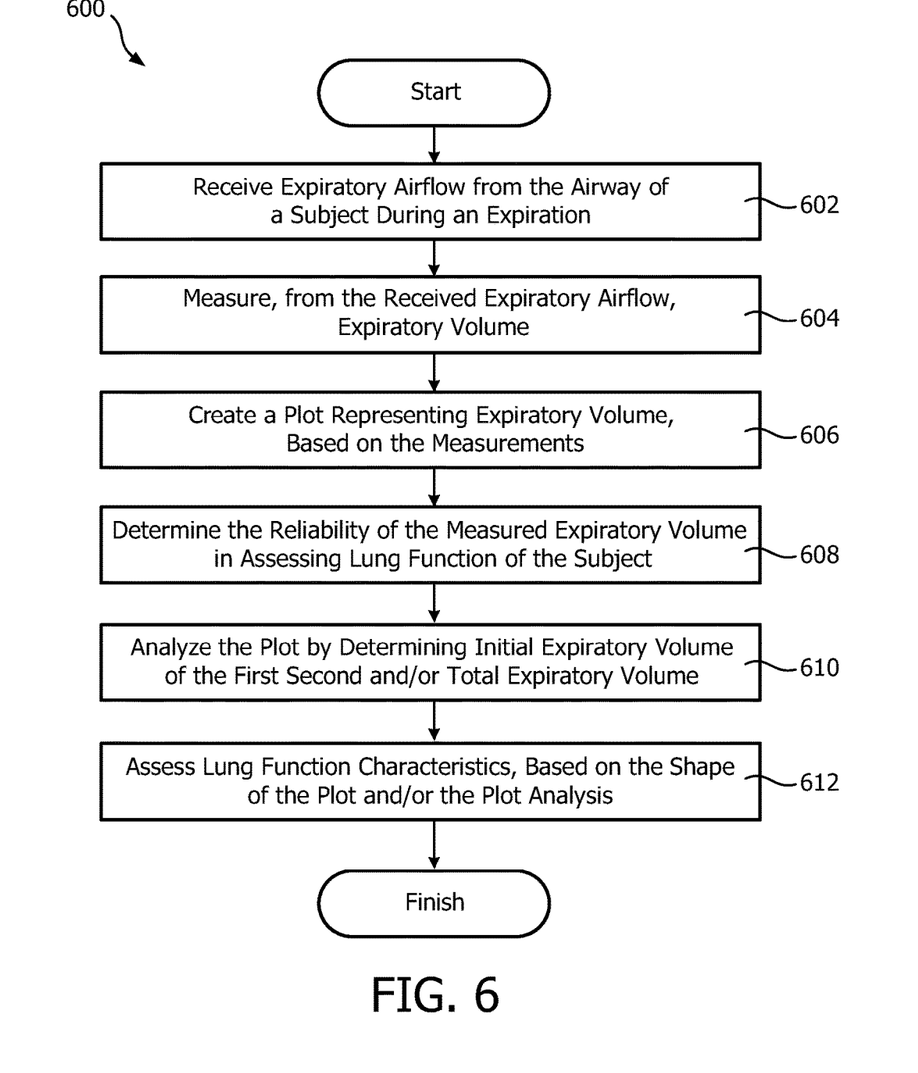
FIG. 6 illustrates a method for assessing lung function of a subject.

FIG. 6 illustrates a method 600 for assessing lung function of a subject. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, expiratory airflow from the airway of a subject during an expiration is received. In one embodiment, operation 602 is performed by a mouthpiece similar to or substantially the same as mouthpiece 144 (shown in FIG. 1 and described above).

At an operation 604, the expiratory volume is measured from the received airflow. In one embodiment, operation 604 is performed by a sensor similar to or substantially the same as sensor 140 (shown in FIG. 1 and described above).

At an operation 606, a plot representing expiratory volume may be created, based on the measured expiratory airflow. In one embodiment, operation 606 is performed by a plotting module similar to or substantially the same as plotting module 111 (shown in FIG. 1 and described above).

At an operation 608, the reliability of the measured expiratory volume in assessing lung function of the subject is determined. In one embodiment, operation 608 is performed by a reliability module, similar to or substantially the same as reliability module 112 (shown in FIG. 1 and described above). In some embodiments, operation 608 is performed, at least partially, by a template-matching module, similar to or substantially the same as template-matching module 115 (shown in FIG. 1 and described above).

At an operation 610, the plot is analyzed by determining the initial expiratory volume of the first second (or period of time that may be less or greater than one second) of the expiration and/or the total expiratory volume. In one embodiment, operation 610 is performed by an analysis module, similar to or substantially the same as analysis module 113 (shown in FIG. 1 and described above).

At an operation 612, lung function characteristics are assessed, based on the shape of the plot and/or the plot analysis performed in operation 610. In one embodiment operation 612 is performed by an assessment module, similar to or substantially the same as assessment module 114 (shown in FIG. 1 and described above). In some embodiments, operation 612 is performed, at least partially, by a template-matching module, similar to or substantially the same as template-matching module 115 (shown in FIG. 1 and described above).

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for reducing computational resource usage for computer-assisted lung function diagnosis, the method comprising:
   receiving, with one or more physical processors, measurements of expiratory volume of a subject during an expiration by the subject for a test;
   creating a plot representing the measurements of expiratory volume of the subject;
   determining, with one or more physical processors, shape templates associated with the test, wherein each of the shape templates represents expiratory volume measurements that are unreliable for the test;
   determining, with one or more physical processors, whether to perform an automated interpretation process on the plot representing the measurements of expiratory volume of the subject such that:
   (i) responsive to a shape representative of the plot corresponding to at least one of the shape templates associated with the test, performance of the automated interpretation process on the plot to generate a diagnosis for the subject is avoided; and
   (ii) responsive to the shape representative of the plot not corresponding to any of the shape templates associated with the test, the automated interpretation process is performed on the plot by one or more physical processors to generate the diagnosis for the subject, wherein the automated interpretation process is configured to interpret expiratory volume measurements with respect to the test to generate the diagnosis, the diagnosis comprising an assessment regarding a lung function of the subject.

2. The method of claim 1, further comprising:
   adjusting, with one or more physical processors, the shape templates associated with the test based on one or more of a gender, age, height, weight, or ethnic background of the subject, wherein performance of the automated interpretation process on the plot to generate the diagnosis for the subject is avoided responsive to the shape representative of the plot corresponding to at least one of the adjusted shape templates, and wherein the automated interpretation process is performed on the plot by one or more physical processors to generate the diagnosis for the subject responsive to the shape representative of the plot not corresponding to any of the adjusted shape templates.

3. The method of claim 1, wherein the shape templates associated with the test includes plotted representations of sub-maximal expiratory effort, a delay in initiation of expiration, a shortening of expiratory duration, a delay in reaching maximum expiratory flow rate, coughing during expiration, glottic obstruction, and/or air leakage.

4. The method of claim 1, further comprising:
determining, with one or more physical processors, shape templates associated with lung diseases, wherein each of the shape templates represents expiratory volume measurements for a lung disease, wherein:
the automated interpretation process comprises determining whether the shape representative of the plot corresponds to any of the shape templates associated with lung diseases, and
the shape templates associated with lung diseases includes plotted representations of an obstructive lung disease, a restrictive lung disease, and/or a combined obstructive-restrictive lung disease.

5. The method of claim 1, further comprising:
determining, with one or more physical processors, a matching quantifier indicating a degree to which the shape representative of the plot matches one of the shape templates associated with the test; and
determining, with one or more physical processors, that the shape representative of the plot does not correspond to any of the shape templates associated with the test responsive to the matching quantifier not satisfying a matching quantifier threshold level.

6. A system for reducing computational resource usage for computer-assisted lung function diagnosis, the system comprising: one or more physical processors configured by machine readable instructions to:
receive measurements of expiratory volume of a subject during an expiration by the subject for a test;
create a plot representing the measurements of the expiratory volume of the subject;
determine shape templates associated with the test, wherein each of the shape templates represents expiratory volume measurements that are unreliable for the test;
determine whether to perform an automated interpretation process on the plot representing the measurements of expiratory volume of the subject such that:
(i) responsive to a shape representative of the plot corresponding to at least one of the shape templates associated with the test, performance of the automated interpretation process on the plot to generate a diagnosis for the subject is avoided, and
(ii) responsive to the shape representative of the plot not corresponding to any of the shape templates associated with the test, the automated interpretation process is performed on the plot by one or more physical processors to generate the diagnosis for the subject, wherein the automated interpretation process is configured to interpret expiratory volume measurements with respect to the test to generate the diagnosis, the diagnosis comprising an assessment regarding a lung function of the subject.

7. The system of claim 6, wherein the one or more processors are configured to adjust the shape templates associated with the test based on one or more of a gender, age, height, weight, or ethnic background of the subject, wherein performance of the automated interpretation process on the plot to generate the diagnosis for the subject is avoided responsive to the shape representative of the plot corresponding to at least one of the adjusted shape templates, and wherein the automated interpretation process is performed on the plot by one or more physical processors to generate the diagnosis for the subject responsive to the shape representative of the plot not corresponding to any of the adjusted shape template.

8. The system of claim 6, wherein the shape templates associated with the test includes plotted representations of sub-maximal expiratory effort, a delay in initiation of expiration, a shortening of expiratory duration, a delay in reaching maximum expiratory flow rate, coughing during expiration, glottic obstruction, and/or air leakage.

9. The system of claim 6, wherein the one or more physical processors are configured to determine shape templates associated with lung diseases, wherein each of the shape templates represents expiratory volume measurements for a lung disease, and wherein:
the automated interpretation process comprises determining whether the shape representative of the plot corresponds to any of the shape templates associated with lung diseases, and
the shape templates associated with lung diseases includes plotted representations of an obstructive lung disease, a restrictive lung disease, and/or a combined obstructive-restrictive lung disease.

10. The system of claim 6, wherein the one or more physical processors are configured to:
determine a matching quantifier indicating a degree to which the shape representative of the plot matches one of the shape templates associated with the test; and
determining, with one or more physical processors, that the shape representative of the plot does not correspond to any of the shape templates associated with the test responsive to the matching quantifier not satisfying a matching quantifier threshold level.

11. A tangible, non-transitory, machine-readable media storing instructions that, when executed by one or more physical processors, effectuate operations comprising:
receiving measurements of expiratory volume of a subject during an expiration by the subject for a test;
creating a plot representing the measurements of expiratory volume of the subject;
determining shape templates associated with the test, wherein each of the shape templates represents expiratory volume measurements that are unreliable for the test;
determining whether to perform an automated interpretation process on the plot representing the measurements of expiratory volume of the subject such that:
(i) responsive to a shape representative of the plot corresponding to at least one of the shape templates associated with the test, performance of the automated interpretation process on the plot to generate a diagnosis for the subject is avoided; and
(ii) responsive to the shape representative of the plot not corresponding to any of the shape templates associated with the test, the automated interpretation process is performed on the plot by one or more physical processors to generate the diagnosis for the subject, wherein the automated interpretation process is configured to interpret expiratory volume measurements with respect to the test to generate the diagnosis, the diagnosis comprising an assessment regarding a lung function of the subject.

12. The tangible, non-transitory media of claim 11, wherein the operations comprise: adjusting the shape templates associated with the test based on one or more of a gender, age, height, weight, or ethnic background of the subject, wherein performance of the automated interpretation process on the plot to generate the diagnosis for the subject is avoided responsive to the shape representative of the plot corresponding to at least one of the adjusted shape templates, and wherein the automated interpretation process is performed on the plot by one or more physical processors to generate the diagnosis for the subject responsive to the shape representative of the plot not corresponding to any of the adjusted shape templates.

13. The tangible, non-transitory media of claim 11, wherein the shape templates associated with the test include plotted representations of sub-maximal expiratory effort, a delay in initiation of expiration, a shortening of expiratory duration, a delay in reaching maximum expiratory flow rate, coughing during expiration, glottic obstruction, and/or air leakage.

14. The tangible, non-transitory media of claim 11, wherein the operations comprise:
   determining shape templates associated with lung diseases, wherein each of the shape templates represents expiratory volume measurements for a lung disease, wherein:
      the automated interpretation process comprises determining whether the shape representative of the plot corresponds to any of the shape templates associated with lung diseases, and
      the shape templates associated with lung diseases include plotted representations of an obstructive lung disease, a restrictive lung disease, and/or a combined obstructive-restrictive lung disease.

15. The tangible, non-transitory media of claim 11, wherein the operations comprise:
   determining, with one or more physical processors, a matching quantifier indicating a degree to which the shape representative of the plot matches one of the shape templates associated with the test; and
   determining, with one or more physical processors, that the shape representative of the plot does not correspond to any of the shape templates associated with the test responsive to the matching quantifier not satisfying a matching quantifier threshold level.

* * * * *